United States Patent [19]
Baak et al.

[11] Patent Number: 6,066,745
[45] Date of Patent: May 23, 2000

[54] PROCESS FOR THE SYNTHESIS OF VITAMIN E

[75] Inventors: Marcel Baak, Ins, Switzerland; Werner Bonrath, Freiburg, Germany; Paul Kreienbühl, Riehen, Switzerland

[73] Assignee: Roche Vitamins Inc., Nutley, N.J.

[21] Appl. No.: 09/282,411

[22] Filed: Mar. 31, 1999

[30] Foreign Application Priority Data

Apr. 6, 1998 [EP] European Pat. Off. .............. 98106237

[51] Int. Cl.$^7$ ................................. C07D 311/72
[52] U.S. Cl. ............................................ 549/408
[58] Field of Search ............................................. 549/408

[56] References Cited

U.S. PATENT DOCUMENTS

| | | |
|---|---|---|
| 2,411,969 | 12/1946 | Karrer . |
| 2,723,278 | 11/1955 | Surmatis et al. . |
| 3,708,505 | 1/1973 | Greenbaum et al. . |

FOREIGN PATENT DOCUMENTS

| | | |
|---|---|---|
| 0694541 | 1/1996 | European Pat. Off. . |
| 1204840 | 9/1970 | United Kingdom . |
| 97/28151 | 8/1997 | WIPO . |
| WO 97/28151 | 8/1997 | WIPO . |

OTHER PUBLICATIONS

M. Kajiwara, et al., "The Synthesis of Regiospecifically $^{13}$C–Labeled α–Tocopheryl Acetate," Heterocycles vol. 15, No. 2, pp. 1209–1212 (1981).

S. Urano and M. Matsuo, "The Synthesis of C–13 Labeled Vitamin E, [2a–$^{13}$C] all–rac–α–Tocopherol$^1$" Heterocycles, vol. 22, No. 9, pp. 1975–1977 (1984).

International Search Report dated May 30, 1997 corresponding to PCT/EP97/00324 (WO 97/28151).

*Primary Examiner*—Johann Richter
*Assistant Examiner*—Taofiq A. Solola
*Attorney, Agent, or Firm*—Mark E. Waddell; Stephen M. Haracz; Bryan Cave LLP

[57] ABSTRACT

A process for the manufacture of d,1-α-tocopherol by the acid catalyzed condensation of trimethylhydroquinone with isophytol is provided, in which the condensation is carried out in the presence of not more than about 0.4 weight percent, based on the weight of isophytol, of a sulfur-containing acid catalyst such as sulfuric acid, methanesulphonic acid, ethanesulphonic acid, trifluoromethanesulphonic acid, p-toluenesulphonic acid, fluorosulphonic acid and mixtures thereof, and in a solvent which is ethylene or propylene carbonate or a mixture of both carbonates, or a mixture of one or both of the carbonates and a non-polar solvent.

29 Claims, No Drawings

PROCESS FOR THE SYNTHESIS OF VITAMIN E

FIELD OF THE INVENTION

The present invention relates to a process for the manufacture of d,1-α-tocopherol.

BACKGROUND OF THE INVENTION

As is known, d,1-α-tocopherol is a diastereoisomeric mixture of 2,5,7,8-tetramethyl-2-(4',8',12'-trimethyl-tridecyl)-6-chromanol (α-tocopherol), which is the most active and industrially most important member of the vitamin E group.

Many processes for the manufacture of d,1-α-tocopherol by the condensation of trimethylhydroqllinone (TMHQ) with isophytol (IP) in the presence of various catalysts or catalyst systems and in various solvents are described in the literature. These processes go back to the work of Karrer et al., Bergel et al. as well as Smith et al.: see Helv. Chim. Acta 21, 520 et seq. (1938), Nature 142, 36 et seq. (1938); Science 88, 37 et seq. (1938); and J. Am. Chem. Soc. 61, 2615 et seq. (1939).

While Karrer et al. carried out the synthesis of d,1-α-tocopherol from TMHQ and phytyl bromide in the presence of anhydrous zinc chloride ($ZnCl_2$, a Lewis acid), not only Bergel et al. but also Smith et al. used TMHQ and phytol as starting materials. In the following years mainly modifications, e.g. alternative solvents and Lewis acids, were developed. From the work of Karrer et al., a process for the manufacture of d,1-α-tocopherol was developed in 1941 in which the condensation of TMHQ with IP was carried out in the presence of a $ZnCl_2$/hydrochloric acid (HCl) catalyst system: see U.S. Pat. No. 2,411,969. Later publications, e.g. Japanese Patent Publications (Kokai) 54380/1985, 64977/1985 and 226979/1987 [Chemical Abstracts (C.A.) 103, 123731s (1985), C.A. 103, 104799d (1985) and C.A. 110, 39217r (1989)], describe this condensation in the presence of zinc, $ZnCl_2$ and a Bronsted (protonic) acid such as a hydrohalic acid, e.g. HCl, trichloroacetic acid, acetic acid and the like, especially $ZnCl_2$/HCl, as the catalyst system.

Disadvantages of these and further published processes featuring $ZnCl_2$ in combination with a Bronsted acid include the corrosive properties of the acids and the contamination of the waste water with zinc ions as a result of the large amount of $ZnCl_2$ required for the catalysis.

The manufacture of d,1-α-tocopherol by the reaction of TMHQ with phytyl chloride, phytol or isophytol in the presence of boron trifluoride ($BF_3$) or its etherate ($BF_3.Et_2O$) is described in German Patent Nos. 960720 and 1015446, as well as in U.S. Pat. Nos. 3,444,213 and 4,634,781. These reactions are not ideal because $BF_3$ also has corrosive properties.

Furthermore, the condensation of TMHQ with IP or another phytyl derivative in the presence of a Lewis acid, e.g. $ZnCl_2$, $BF_3$ or aluminum trichloride ($AlCl_3$), a strong acid, e.g. HCl, and an amine salt as the catalyst system is described in European Patent Publication (EP) 100471. In an earlier patent publication, DOS 2606830, the IP or phytol is pretreated with ammonia or an amine before the condensation with TMHQ in the presence of $ZnCl_2$ and an acid is effected. In both cases, corrosion problems occur which diminish the usefulness of these reactions.

A further method for the manufacture of d,1-α-tocopherol from TMHQ and IP includes using an isolated TMHQ-$BF_3$ or -$AlCl_3$ complex as the catalyst and a solvent mixture featuring a nitro compound (DOS 1909164). This process avoids to a large extent the formation of undesired by-products because it involves mild reaction conditions. The yield of d,1-α-tocopherol, based on IP and the use of the solvent mixture methylene chloride/nitromethane, is given as 77%. However, the use of such a solvent mixture is disadvantageous.

The manufacture of d,1-α-tocopherol by the condensation of TMHQ with IP using cation exchange complexes of metal ions ($Zn^{2+}$, $Sn^{2+}$ and $Sn^{4+}$) is disclosed in Bull. Chem. Soc. Japan 50, 2477–2478 (1977). Among other disadvantages, these reactions produce unsatisfactory yields.

The use of macroreticular ion exchangers, e.g. Amberlyst® 15 as the catalyst for the condensation of TMHQ with IP, is described in U.S. Pat. No. 3,459,773.

EP 603695 describes the manufacture of d,1-α-tocopherol in liquid or supercritical carbon dioxide by the condensation of TMHQ with IP in the presence of acidic catalysts, such as $ZnCl_2$/HCl and ion exchangers.

The condensation reaction which takes place in the presence of a catalyst system containing iron(II) chloride, metallic iron and HCl gas is described in DOS 2160103 and U.S. Pat. No. 3,789,086. These reactions form fewer byproducts compared with the aforementioned process using $ZnCl_2$/HCl. These reactions, however, are prone to corrosion problems and chloride contamination.

An alternative to the condensation of TMHQ with IP to d,1-α-tocopherol includes using trifluoroacetic acid or its anhydride as the catalyst (EP 12824). Although this process avoids the use of HCl, the alternative catalyst is relatively expensive, and thus not commercially viable.

The use of heteropolytungsten acids as catalysts for the condensation of TMHQ with IP was described for the first time in React. Kinet. Catal. Lett. 47(1), 59–64 (1992). In these reactions, d,1-α-tocopherol was reportedly obtained in about 90% yield using various solvents.

A further process described in EP 658552; Bull. Chem. Soc. Japan 68, 3569–3571 (1995) for the synthesis of d,1-α-tocopherol is based on the use of a scandium, yttrium or lanthanide fluorosulphonate, nitrate or sulfate, e.g. scandium trifluoromethanesulphonate. When up to about 10% excess of IP is used, this process reportedly provides yields up to 98%.

The use of ion exchanged bentonite, montmorillonite or saponite through treatment with, e.g. scandium chloride and other metal salts (yttrium, lanthanum, etc.) as the catalyst for the condensation of TMHQ with IP has been described. Such a reaction is disadvantageous because of the need for a large amount of catalyst: see EP 677520; Bull. Chem. Soc. Japan 69, 137–139 (1996).

According to the Examples of EP 694 541, the condensation of TMHQ with IP to form α-tocopherol reportedly can be achieved in high yields and with a high product purity when solvents such as carbonate esters, fatty acid esters and mixed solvent systems are employed. In these reactions, catalysis is effected by $ZnCl_2$/HCl. These reactions suffer from several drawbacks, including contamination of the waste water by zinc ions and the requirement for the use of large "catalyst amounts" of $ZnCl_2$.

According to WO 97/28151, the acid-catalyzed condensation of TMHQ with IP can reportedly be performed using a cyclic carbonate or α-lactone as the solvent. The preferred catalyst is a mixture of ortho boric acid and oxalic, tartaric or citric acid, or boron trifluoride etherate.

In summary, all the reactions producing d,1-α-tocopherol described in the references cited above suffer from considerable disadvantages, including corrosion problems when acid catalysts such as boron trifluoride are used; toxicity problems when boron trifluoride adducts are used; and contamination of the waste water with metal ions when iron or zinc is used. Moreover, in some of the processes set forth above, the formation of undesired byproducts, e.g. phytyltoluene and chlorophytols, is an especially serious problem.

SUMMARY OF THE INVENTION

The present invention is a process for the manufacture of d,1-α-tocopherol by the acid-catalyzed condensation of trimethylhydroquinone with isophytol in the presence of at most 0.4 weight percent based on the weight of isophytol of a sulphur-containing acid catalyst. The sulphur-containing acid catalyst is preferably selected from sulfuric acid, methanesulphonic acid, ethanesulphonic acid, trifluoromethanesulphonic acid, p-toluenesulphonic acid, fluorosulphonic acid and mixtures thereof. Furthermore, the condensation is effected in a one-phase solvent system, the solvent being selected from ethylene carbonate, propylene carbonate and mixtures thereof, or in a two-phase solvent system, the solvent being selected from a mixture of a non-polar solvent with ethylene carbonate, propylene carbonate or a mixture of these carbonates.

It is an object of the present invention to provide a process for the manufacture of d,1-α-tocopherol by the condensation of trimethylhydroquinone with isophytol in the presence of a catalyst and in a solvent, in which process there is no, or at least a much reduced, corrosive action. It is another object of the present invention that the process be non-toxic and does not contaminate the environment.

It is a further object of the present invention that the catalyst used catalyzes the reaction selectively and in high yields. It is another object of the invention that the catalyst be suitably active in small, catalytic amounts, be readily separable after the reaction and be re-usable.

The present invention will be more fully understood by a reading of the section entitled "Detailed Description of the Invention".

DETAILED DESCRIPTION OF THE INVENTION

The present invention is a process for carrying out the condensation of trimethylhydroquinone with isophytol in the presence of not more than about 0.4 weight percent, based on the weight of isophytol, of a sulfur-containing acid catalyst.

The condensation reaction of the present invention is represented in the following Reaction Scheme:

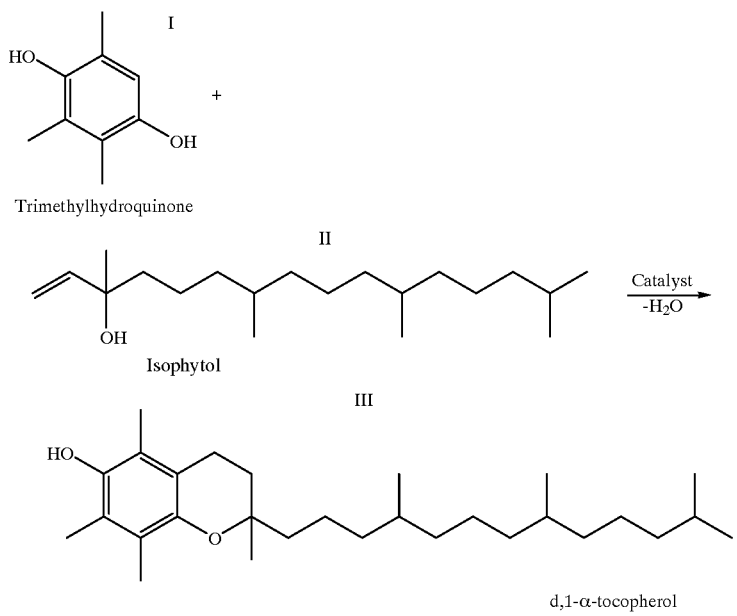

The process of the present invention has utility in the manufacture of d,1-α-tocopherol by the acid-catalyzed condensation of trimethylhydroquinone with isophytol in a one-phase or two-phase solvent system. As used herein, a one-phase solvent system contains a carbonate solvent such as ethylene carbonate, propylene carbonate or a mixture thereof. A two-phase solvent system has as its first phase a non-polar solvent and as its second phase a carbonate solvent such as ethylene carbonate, propylene carbonate or a mixture thereof.

The expression "sulfur-containing acid catalyst" as used herein means any acid which features sulfur in the oxidation state or level 6; a sulfur atom in the oxidation state or level 6 is commonly designated S (VI).

For the purposes of the present invention, the non-polar solvent is suitably an aliphatic hydrocarbon such as, for example, hexane, heptane or petroleum ether, preferably heptane.

In the process of the present invention, the condensation reaction is carried out in the presence of no more than about 0.4 weight percent, based on the weight of isophytol, of a sulfur-containing acid catalyst. In the present invention, the amount of sulfur-containing acid catalyst present in the reaction is from about 0.1 to about 0.4 weight percent, preferably from about 0.1 to about 0.2 weight percent, based on the weight of isophytol. The weight of isophytol is the amount introduced to the reaction mixture as a starting material. The acid catalyst used to effect the process of the present invention is preferably selected from sulfuric acid, methanesulphonic acid, ethanesulphonic acid, trifluoromethanesulphonic acid, p-toluene sulphonic acid, fluorosulphonic acid and mixtures thereof. The acid catalyst is more preferably sulfuric acid or p-toluenesulphonic acid. The use of such sulfur-containing acid catalysts renders the use of a Lewis acid unnecessary.

In the present invention, trimethylhydroquinone is conveniently used in a molar excess over isophytol of about 30% to 65%, preferably about 50%. These amounts represent amounts of the respective starting materials introduced to the reaction mixture.

The condensation reaction of the present invention is conveniently effected at temperatures from about 50° C. to about 150° C., preferably from about 80° C. to about 120° C., most preferably at about 100° C.

When the reaction of the present invention is carried out in the presence of a two-phase solvent system, then the volume ratio of the non-polar solvent to the carbonate used in the two-phase solvent system is conveniently in the range from about 0.3:1 to about 5:1.

In the present invention, the total amount of carbonate-based solvent, i.e. ethylene carbonate and/or propylene carbonate, is conveniently from about 10 to about 100 ml, preferably from about 10 to about 50 ml, per 100 mmol of trimethylhydroquinone. When a non-polar solvent is additionally used, i.e., in the two-phase solvent system, about 50 to about 150 ml, preferably about 70 to about 120 ml, of the non-polar solvent is used per 100 mmol of isophytol introduced to the reaction mixture. Preferably, only one or the other carbonate solvent is used, either as the sole solvent or as the carbonate-component of the two-phase solvent system. In the two-phase solvent system, heptane and ethylene carbonate are the preferred solvents.

The condensation reaction of the present invention is preferably carried out under an inert gas atmosphere, such as for example, in a gaseous nitrogen or argon environment.

The process of the invention can be carried out operationally in a very simple manner by adding isophytol alone, or a solution of isophytol in the optionally employed non-polar solvent, dropwise to a solution or suspension of the trimethylhydroquinone and the acid catalyst in ethylene or propylene carbonate or a mixture thereof. The rate at which the isophytol is added is not critical. For example, isophytol is added dropwise over a period of 0.1 hour to 1 hour, preferably 0.3 hour to 0.5 hour. After completion of the isophytol addition and the subsequent condensation reaction, during which it is advantageous to remove the resulting water by azeotropic distillation or in the flow of inert gas thereover (i.e., over the reactants), isolation and purification of the obtained d,1-α-tocopherol can be effected by procedures conventionally used in organic chemistry, such as for example, by distillation.

Particular advantages in the use of the acid catalyst in the process in accordance with the present invention are, in addition to high yields of d,1-α-tocopherol, the avoidance of waste water contamination with heavy metal ions, high selectivity, as well as ready isolation of the d,1-α-tocopherol product from the mixture after reaction, in particular from the unreacted trimethylhydroquinone.

The following examples are provided to further illustrate the processes of the present invention. These examples are illustrative only and are not intended to limit the scope of the invention in any way.

EXAMPLE 1

To a mixture of 23.3 g (150 mmol) of 2,3,5-trimethylhydroquinone (98% pure), 80 ml of ethylene carbonate (99% pure) and 0.14 ml of 10% (v/v) sulfuric acid (0.25 mmol), a solution of 31.21 g (100 mmol) of isophytol (95% pure) in 100 ml of heptane was added dropwise under an argon atmosphere and with stirring at 100° C. over a period of 20 minutes. During the addition of isophytol an azeotropic mixture of water/heptane was separated with the help of a water separator. After completion of the addition, the reaction mixture was stirred for another 30 minutes with removal of heptane. The internal temperature rose to about 145° C. After cooling the reaction mixture to about 90° C., 200 ml of heptane were added and the mixture was stirred for about 5 minutes. The upper layer was separated and the lower carbonate layer was extracted with a further 100 ml of heptane. The combined heptane layers were washed with 20 ml of water. After removal of heptane by evaporation, 43.76 g (95.6% yield) of d,1-α-tocopherol were obtained as a brown oil with a purity, as determined by gas chromatographic (GC) analysis, of 94.1%.

EXAMPLE 2

To a mixture of 23.3 g (150 mmol) of 2,3,5-trimethylhydroquinone (98% pure), 80 ml of ethylene carbonate (99% pure) and 0.28 ml of 10% (v/v) sulfuric acid (0.50 mmol), a solution of 31.21 g (100 mmol) of isophytol (95% pure) in 100 ml of heptane was added dropwise under an argon atmosphere with stirring at 100° C. over a period of 20 minutes. During the addition of isophytol an azeotropic mixture of water/heptane was separated with the help of a water separator. After completion of the addition, the reaction mixture was stirred for another 30 minutes with removal of heptane. The internal temperature rose to about 145° C. After cooling the reaction mixture to about 90° C., 200 ml of heptane were added and the mixture was stirred for about 5 minutes. The upper layer was separated and the lower carbonate layer was extracted with a further 100 ml of heptane. The combined heptane layers were washed with 20 ml of water. After removal of heptane by evaporation 43.71 g (95.6% yield) of d,1-α-tocopherol were obtained as a brown oil with a purity, according to GC analysis, of 94.2%.

EXAMPLE 3

To a mixture of 93.18 g (600 mmol) of 2,3,5-trimethylhydroquinone (98% pure), 80 ml of ethylene carbonate (99% pure) and 1.12 ml of 10% (v/v) sulfuric acid (2.0 mmol), a solution of 124.85 g (400 mmol) of isophytol (95% pure) in 400 ml of heptane was added dropwise under an argon atmosphere with stirring at 100° C. over a period of 20 minutes. During the addition of isophytol an azeotropic mixture of water/heptane was separated with the help of a water separator. After completion of the addition, the reaction mixture was stirred for another 30 minutes with removal of heptane. The internal temperature rose to about 145° C. After cooling the reaction mixture to about 90° C., 200 ml of heptane were added and the mixture was stirred for about 5 minutes. The upper layer was separated and the lower carbonate layer was extracted with a farther 100 ml of heptane. The combined heptane layers were washed with 20 ml of water. After evaporation of the heptane, 174.84 g (95.6% yield) of d,1-α-tocopherol were obtained as a brown oil with a purity, according to GC analysis, of 94.2%.

EXAMPLES 4–9

In a flask with reflux condenser, water collector and mechanical stirrer, 23.3 g (150 mmol) of 2,3,5-trimethylhydroquinone (98% pure) and an acid catalyst as indicated in Table 1 (p-TsOH=p-toluenesulphonic acid)

were dissolved in 80 ml of ethylene carbonate. A solution of 36.55 ml (100 mmol) of isophytol (96% pure) in 100 ml of heptane was added within 30 minutes at about 100° C. and the reaction mixture was heated for 30 minutes with removal of heptane. The mixture was then heated at 135° C. for 30 minutes. The resulting two-phase system was cooled to 80° C., and 100 ml of heptane were added. The two phases were separated and the lower carbonate layer was re-used. The upper heptane layer was concentrated under reduced pressure. The isolated crude d,1-α-tocopherol product was analyzed by GC to determine the purity. The acid catalysts used and results obtained are summarized in Table 1 below:

TABLE 1

| Example | Catalyst (weight % based on IP) | Yield (%) | Purity (%) |
|---|---|---|---|
| 4 | p-TsOH (0.13) | 92.0 | 87.0 |
| 5 | $H_2SO_4$ (0.25) | 93.3 | 89.6 |
| 6 | $C_2H_5SO_3H$ (0.33) | 91.8 | 88.4 |
| 7 | $CH_3SO_3H$ (0.35) | 95.0 | 90.8 |
| 8 | $CF_3SO_3H$ (0.37) | 95.7 | 89.7 |
| 9 | $FSO_3H$ (0.12) | 92.1 | 86.4 |

EXAMPLE 10

In a flask with reflux condenser, water collector and mechanical stirrer 23.3 g (150 mmol) of 2,3,5-trimethylhydroquinone (98% pure) and 0.1 g of p-toluenesulphonic acid were dissolved in 80 ml of propylene carbonate. A solution of 36.55 ml (100 mmol) of isophytol (96% pure) in 100 ml of hexane was added within 30 minutes at about 100° C. and the reaction mixture was heated for 30 minutes while removing the hexane. The mixture was then heated at 135° C. for 30 minutes. The resulting two-phase system was cooled to 80° C. and 100 ml of hexane were added. The two phases were separated and the lower carbonate layer was re-used. The upper hexane layer was concentrated under reduced pressure and yielded 39.75 g (92.3% yield) of crude d,1-α-tocopherol with a purity, according to GC analysis, of 87.0%.

EXAMPLE 11

In a flask with a reflux condenser, a water collector and a mechanical stirrer, 23.3 g (150 mmol) of 2,3,5-trimethylhydroquinone (98% pure) and 0.1 g of p-toluenesulphonic acid were dissolved in 80 ml of ethylene carbonate. A solution of 36.55 ml (100 mmol) of isophytol (96%) was added within 30 minutes at about 100° C. and the reaction mixture was heated for 30 minutes. The reaction solution was then heated at 135° C. for 30 minutes and cooled to 80° C. The two phases were separated; the upper layer consisted of 39.23 g (91.1% yield) of crude d,1-α-tocopherol with a purity (according to GC analysis) of 87.1%.

The invention being thus described, one skilled in the art can ascertain that the same may be varied in many ways. Such variations are not to be regarded as a departure from the spirit and scope of the invention and all such modifications are intended to be included within the scope of the following claims.

What is claimed is:

1. A process for making d,1-α-tocopherol by an acid-catalyzed condensation reaction comprising:
carrying out a condensation reaction of trimethylhydroquinone and isophytol in the presence of up to 0.4 weight percent, based on the weight of isophytol, of a sulfur-containing acid catalyst and a one-phase solvent system consisting essentially of a carbonate solvent selected from the group consisting of ethylene carbonate, and propylene carbonate or mixtures thereof, or a two-phase solvent system consisting essentially of a non-polar solvent and a carbonate solvent selected from the group consisting of ethylene carbonate, and propylene carbonate or mixtures thereof, to provide a mixture resulting from the condensation reaction, wherein the reaction is carried out in the absence of a Lewis acid.

2. The process according to claim 1, wherein the sulfur-containing acid catalyst is selected from the group consisting of sulfuric acid, methanesulphonic acid, ethanesulphonic acid, trifluoromethanesulphonic acid, p-toluenesulphonic acid, and fluorosulphonic acid or mixtures thereof.

3. The process according to claim 2, wherein the catalyst is selected from the group consisting of sulfuric acid and p-toluenesulphonic acid.

4. The process according to claim 1, wherein the sulfur-containing acid catalyst is present in an amount from about 0.1 to about 0.4 weight percent based on the weight of the isophytol.

5. The process according to claim 4, wherein the acid catalyst is present in an amount from about 0.1 to about 0.2 weight percent based on the weight of isophytol.

6. The process according to claim 1, wherein the one-phase solvent system is ethylene carbonate.

7. The process according to claim 1, wherein the two-phase solvent system consists essentially of a mixture of ethylene carbonate and a non-polar solvent.

8. The process according to claim 1, wherein the non-polar solvent is selected from the group consisting of hexane, heptane, and petroleum ether or mixtures thereof.

9. The process according to claim 8, wherein the non-polar solvent is heptane.

10. The process according to claim 1, wherein the volume ratio of the non-polar solvent to the carbonate solvent in the two-phase system is from about 0.3:1 to about 5:1.

11. The process according to claim 1, wherein the condensation reaction is carried out at from about 50° C. to about 150° C.

12. The process according to claim 11, wherein the condensation reaction is carried out at from about 80° C. to about 120° C.

13. The process according to claim 12, wherein the condensation reaction is carried out at about 100° C.

14. The process according to claim 1, wherein trimethylhydroquinone is in an amount which is a molar excess over isophytol of about 30% to 65%.

15. The process according to claim 14, wherein trimethylhydroquinone is in an amount which is a molar excess over isophytol of about 50%.

16. The process according to claim 1, wherein the condensation reaction is carried out in an inert gas atmosphere.

17. The process according to claim 16, wherein the inert gas atmosphere is gaseous nitrogen or argon.

18. The process according to claim 1, wherein the condensation reaction is carried out with about 10 ml to about 100 ml of the one-phase solvent system per 100 mmol of trimethylhydroquinone.

19. The process according to claim 18, wherein the volume of the one-phase solvent is about 10 ml to about 50 ml per 100 mmol of trimethylhydroquinone.

20. The process according to claim 1, wherein the reaction is carried out with from about 10 ml to about 100 ml of the carbonate solvent per 100 mmol of trimethylhydroquinone and from about 50 ml to about 150 ml of non-polar solvent per 100 mmol of isophytol.

21. The process according to claim 20, wherein the volume of the carbonate solvent is from about 10 ml to about 50 ml per 100 mmol of trimethylhydroquinone, and the volume of the non-polar solvent is from about 70 ml to about 120 ml per 100 mmol of isophytol.

22. The process according to claim 1, further comprising adding isophytol or a solution of isophytol in the non-polar solvent dropwise to a solution or suspension of trimethylhydroquinone and the sulfur-containing acid catalyst in the carbonate solvent.

23. The process according to claim 1, further comprising removing water from the mixture during the condensation reaction by azeotropic distillation or in the flow of inert gas.

24. A process for making d,1-α-tocopherol by a non Lewis acid-catalyzed condensation reaction, comprising the steps of:
   (a) adding a solution comprising isophytol to a solution or suspension consisting essentially of trimethylhydroquinone, a sulfur-containing acid catalyst and a carbonate solvent selected from the group consisting of ethylene carbonate, propylene and carbonate or mixtures thereof, wherein the amount of the sulfur-containing acid catalyst is up to 0.4 weight percent, based on the weight of isophytol, to provide a reaction mixture; and
   (b) heating the reaction mixture.

25. The process according to claim 24, wherein the sulfur-containing acid catalyst is selected from the group consisting of sulfuric acid, methanesulphonic acid, ethanesulphonic acid, trifluoromethanesulphonic acid, p-tolunesulphonic acid, and fluorosulphonic acid or mixtures thereof.

26. The process according to claim 24, wherein the solution comprising isophytol consists essentially of isophytol and a non-polar solvent.

27. The process according to claim 24, wherein the solution comprising isophytol consists essentially of isophytol.

28. A process for making d,1-α-tocopherol by an acid-catalyzed condensation reaction according to claim 1 further comprising isolating d,1-α-tocopherol from the mixture.

29. A process for making d,1-α-tocopherol by an acid-catalyzed condensation reaction according to claim 24 further comprising isolating d,1-α-tocopherol from the mixture.

* * * * *